(12) United States Patent
Ewert et al.

(10) Patent No.: US 8,344,198 B2
(45) Date of Patent: Jan. 1, 2013

(54) PROCESS TO DECREASE OR ELIMINATE CORROSION FROM THE DECOMPOSITION OF HALIDE CONTAINING OLEFIN CATALYSTS

(75) Inventors: Warren M. Ewert, Bartlesville, OK (US); Bruce E. Kreischer, Kingwood, TX (US); Ronald D. Knudsen, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 1971 days.

(21) Appl. No.: 10/800,471

(22) Filed: Mar. 15, 2004

(65) Prior Publication Data

US 2004/0236163 A1   Nov. 25, 2004

Related U.S. Application Data

(60) Provisional application No. 60/455,217, filed on Mar. 14, 2003.

(51) Int. Cl.
*C07C 2/08* (2006.01)
*B08B 9/00* (2006.01)

(52) U.S. Cl. ........ 585/512; 585/513; 585/520; 585/527; 585/950; 134/22.14; 134/22.19

(58) Field of Classification Search .................. 585/512, 585/520
See application file for complete search history.

(56) References Cited

U.S. PATENT DOCUMENTS

| | | | |
|---|---|---|---|
| 4,668,838 A | 5/1987 | Briggs | |
| 4,777,315 A | 10/1988 | Levine et al. | |
| 4,853,356 A | 8/1989 | Briggs | |
| 5,198,563 A | 3/1993 | Reagen et al. | |
| 5,288,823 A | 2/1994 | Reagen et al. | |
| 5,331,070 A | 7/1994 | Pettijohn et al. | |
| 5,331,104 A | 7/1994 | Reagen et al. | |
| 5,340,785 A | 8/1994 | Reagen et al. | |
| 5,360,879 A | 11/1994 | Reagen et al. | |
| 5,376,612 A | 12/1994 | Reagen et al. | |
| 5,382,738 A | 1/1995 | Reagen et al. | |
| 5,393,719 A | 2/1995 | Pettijohn et al. | |
| 5,399,539 A | 3/1995 | Reagen et al. | |
| 5,438,027 A | 8/1995 | Reagen et al. | |
| 5,451,645 A | 9/1995 | Reagen et al. | |
| 5,470,926 A | 11/1995 | Reagen et al. | |
| 5,491,272 A | 2/1996 | Tanaka et al. | |
| 5,523,507 A | 6/1996 | Reagen et al. | |

(Continued)

FOREIGN PATENT DOCUMENTS

CN   1256968 A   6/2000

(Continued)

OTHER PUBLICATIONS

International Search Report, Jul. 13, 2004, PCT/US04/08189.

*Primary Examiner* — Ellen McAvoy
(74) *Attorney, Agent, or Firm* — Conley Rose, P.C.; Rodney B. Carroll; Lynda S. Jolly (57) ABSTRACT

A processes is provided to inhibit or limit the decomposition of a halide-containing olefin oligomerization catalyst system during recovery of an oligomerization product. The process includes deactivation of an olefin oligomerization catalyst system present in an olefin oligomerization reactor effluent stream by contact with an alcohol under conditions that minimize potential for deactivated catalyst system decomposition. Such conditions include minimization of the water content of the deactivation agent and concentration of the deactivation agent.

15 Claims, 4 Drawing Sheets

U.S. PATENT DOCUMENTS

| | | | |
|---|---|---|---|
| 5,543,375 | A | 8/1996 | Lashier et al. |
| 5,550,305 | A | 8/1996 | Wu |
| 5,557,026 | A | 9/1996 | Tanaka et al. |
| 5,563,312 | A | 10/1996 | Knudsen et al. |
| 5,689,028 | A | 11/1997 | Lashier et al. |
| 5,731,487 | A | 3/1998 | Tamura et al. |
| 5,744,677 | A | 4/1998 | Wu |
| 5,750,816 | A | 5/1998 | Araki et al. |
| 5,750,817 | A | 5/1998 | Tanaka et al. |
| 5,763,723 | A | 6/1998 | Reagen et al. |
| 5,786,431 | A | 7/1998 | Reagen et al. |
| 5,811,618 | A | 9/1998 | Wu |
| 5,814,575 | A | 9/1998 | Reagen et al. |
| 5,856,257 | A | 1/1999 | Freeman et al. |
| 5,856,610 | A | 1/1999 | Tamura et al. |
| 5,856,612 | A | 1/1999 | Araki et al. |
| 5,859,303 | A | 1/1999 | Lashier |
| 5,910,619 | A | 6/1999 | Urata et al. |
| 5,919,996 | A | 7/1999 | Freeman et al. |
| 5,968,866 | A | 10/1999 | Wu |
| 5,986,153 | A | 11/1999 | Kallenbach et al. |
| 6,031,145 | A | 2/2000 | Commereuc et al. |
| 6,103,654 | A | 8/2000 | Commereuc et al. |
| 6,127,301 | A | 10/2000 | Iwanaga et al. |
| 6,133,495 | A | 10/2000 | Urata et al. |
| 6,221,986 | B1 | 4/2001 | Commereuc et al. |
| 6,337,297 | B1 | 1/2002 | Mimura et al. |
| 6,344,594 | B1 | 2/2002 | Sen et al. |
| 6,380,451 | B1 | 4/2002 | Kreischer et al. |
| 6,455,648 | B1 | 9/2002 | Freeman et al. |
| 2001/0023281 | A1 | 9/2001 | Commereuc et al. |
| 2001/0053742 | A1 | 12/2001 | Knudsen et al. |
| 2002/0035029 | A1 | 3/2002 | Yoshida et al. |

FOREIGN PATENT DOCUMENTS

| | | |
|---|---|---|
| EP | 537609 A2 | 4/1993 |
| EP | 0668106 | 8/1995 |
| EP | 1110930 A1 | 6/2001 |
| JP | 06263822 A2 | 9/1994 |
| JP | 07010780 A2 | 1/1995 |
| JP | 07017878 A2 | 1/1995 |
| JP | 07018013 A2 | 1/1995 |
| JP | 07118173 A2 | 5/1995 |
| JP | 07118174 A2 | 5/1995 |
| JP | 07118175 A2 | 5/1995 |
| JP | 07118324 A2 | 5/1995 |
| JP | 07118325 A2 | 5/1995 |
| JP | 07118326 A2 | 5/1995 |
| JP | 07118327 A2 | 5/1995 |
| JP | 07118328 A2 | 5/1995 |
| JP | 07149671 A2 | 6/1995 |
| JP | 07149672 A2 | 6/1995 |
| JP | 07149673 A2 | 6/1995 |
| JP | 07149674 A2 | 6/1995 |
| JP | 07149675 A2 | 6/1995 |
| JP | 07149676 A2 | 6/1995 |
| JP | 07149677 A2 | 6/1995 |
| JP | 07157512 A2 | 6/1995 |
| JP | 07215896 A2 | 8/1995 |
| JP | 08059732 A2 | 3/1996 |
| JP | 08134131 A2 | 5/1996 |
| JP | 08151409 A2 | 6/1996 |
| JP | 08183747 A2 | 7/1996 |
| JP | 08239330 A2 | 9/1996 |
| JP | 08239331 A2 | 9/1996 |
| JP | 08239418 A2 | 9/1996 |
| JP | 08245429 A2 | 9/1996 |
| JP | 08245430 A2 | 9/1996 |
| JP | 08245431 A2 | 9/1996 |
| JP | 10087517 A2 | 9/1996 |
| JP | 08283330 A2 | 10/1996 |
| JP | 08283332 A2 | 10/1996 |
| JP | 08301921 A2 | 11/1996 |
| JP | 08301922 A2 | 11/1996 |
| JP | 08301923 A2 | 11/1996 |
| JP | 08301924 A2 | 11/1996 |
| JP | 08301925 A2 | 11/1996 |
| JP | 08325317 A2 | 12/1996 |
| JP | 08325318 A2 | 12/1996 |
| JP | 08325319 A2 | 12/1996 |
| JP | 08333407 | 12/1996 |
| JP | 09012627 A2 | 1/1997 |
| JP | 09040710 A2 | 2/1997 |
| JP | 09087318 A2 | 3/1997 |
| JP | 09143213 A2 | 6/1997 |
| JP | 09176228 A2 | 7/1997 |
| JP | 09176229 A2 | 7/1997 |
| JP | 09188634 A2 | 7/1997 |
| JP | 09194400 A2 | 7/1997 |
| JP | 09194524 A2 | 7/1997 |
| JP | 11060626 A2 | 8/1997 |
| JP | 09262480 A2 | 10/1997 |
| JP | 09268133 A2 | 10/1997 |
| JP | 09268134 A2 | 10/1997 |
| JP | 09268135 A2 | 10/1997 |
| JP | 10007593 A2 | 1/1998 |
| JP | 10007594 A2 | 1/1998 |
| JP | 10007595 A2 | 1/1998 |
| JP | 10036433 A2 | 2/1998 |
| JP | 10036435 A2 | 2/1998 |
| JP | 10045634 A2 | 2/1998 |
| JP | 10045638 | 2/1998 |
| JP | 10045833 A2 | 2/1998 |
| JP | 10087518 A2 | 4/1998 |
| JP | 10218799 A2 | 8/1998 |
| JP | 11060511 A2 | 3/1999 |
| JP | 02066329 A | 3/2002 |
| JP | 02102710 A | 4/2002 |
| WO | WO-9415940 A1 | 7/1994 |
| WO | WO-01/38270 A1 | 5/2001 |
| WO | WO-01/47839 | 7/2001 |
| WO | WO-01/68572 A1 | 9/2001 |
| WO | WO-01/83447 A2 | 11/2001 |
| WO | WO-0204119 A1 | 1/2002 |
| WO | WO-02/066404 A1 | 8/2002 |
| WO | WO-02/066405 A1 | 8/2002 |
| WO | WO-02/083306 A2 | 10/2002 |

PROCESS TO DECREASE OR ELIMINATE CORROSION FROM THE DECOMPOSITION OF HALIDE CONTAINING OLEFIN CATALYSTS

CROSS REFERENCE TO RELATED APPLICATIONS

This patent application claims priority to U.S. Provisional Application No. 60/455,217, filed Mar. 14, 2003, the disclosure of which is incorporated by reference in its entirety herein.

FEDERALLY SPONSORED RESEARCH

Not applicable.

REFERENCE TO MICROFICHE APPENDIX

Not applicable.

FIELD OF THE INVENTION

This invention relates to a system of catalytic olefin preparation and recovery, deactivated catalyst recovery and diluent recycle. More specifically, the invention relates to methods of deactivating the catalyst in the effluent of the oligomerization reactor under conditions which prevent or decrease the formation of hydrogen halide acids during downstream processing and thereby prevent or decrease process equipment corrosion caused by such acids.

BACKGROUND OF THE INVENTION

Olefins, for example alpha-olefins, referred to as 1-olefins, have many uses. In addition to uses as specific chemicals, alpha-olefins are used in polymerization processes either as a monomer or a comonomer to prepare polyolefins, or polymers. Higher alpha-olefins and other olefins can be produced by contacting lower olefins, for example ethylene, with a catalyst, producing trimers of mono-olefins, dimers of diolefins, or other reaction products in an addition reaction. This reaction or addition of two or more olefins is generally referred to as oligomerization. Trimerization, which is the addition of three olefins, is a subset of the general class of oligomerization reactions. Often, the catalyst system is dispersed in a process solvent, and the reactants, a lower 1-olefin and optionally hydrogen, are fed in as gases. The reaction product or higher olefins dissolve in the process solvent as they are formed. Product olefins and catalyst are removed from the reactor in the process solvent containing them, i.e., in the oligomerization reactor effluent.

Unfortunately, during the production of olefins, a significant reaction co-product can be a polymeric material. Polymer production during the course of olefin preparation is detrimental to the process and reactor because polymer can build up on the interior walls or other portions of the reactor and inhibit heat transfer. Furthermore, any polymer produced needs to be separated from the olefin products stream, and/or a low molecular weight polymer can be formed causing a sticky, glue-like substance throughout the process and reactor.

To prevent polymer formation and potential buildup in that part of the process downstream of the oligomerization reactor resulting from active catalyst in the reactor effluent, systems to deactivate catalyst activity have been developed. In addition to prevention of polymer formation, deactivation of the catalyst system is important to prevent isomerization of the 1-olefin product to undesirable internal, i.e., 2- and higher, olefins, which lowers the product purity. Deactivation of the catalyst system also can remove hazards associated with the air- and water-sensitivity of aluminum alkyls.

There exists a need, therefore, for a deactivation process for use with halide-containing oligomerization catalyst systems, for example, metal halides such as alkylaluminum halide, which reduces or eliminates downstream corrosion.

SUMMARY OF THE INVENTION

In accordance with some embodiments of this invention, a process to inhibit or limit the decomposition of a halide-containing olefin oligomerization catalyst system during recovery of an oligomerization product is provided wherein the process includes the steps of forming an intermediate stream by contacting an olefin oligomerization reactor effluent stream which comprises olefin product(s), catalyst system, polymer(s) and/or oligomer(s) with an alcohol that is soluble in any portion of the reactor effluent stream, wherein the catalyst system comprises a chromium source, a pyrrole-containing compound and metal compound and wherein the alcohol is added in an amount to effect a mole alcohol to mole metal compound ratio between about 2.5 and about 1.5. In some embodiments of the invention, the amount of alcohol added to deactivate the catalyst system is greater than about 1.5 and less than about 2.5 moles per mole metal compound. In some embodiments of the invention, the alcohol is added in an amount to deactivate the catalyst system. In some embodiments of the invention, the amount of alcohol added to deactivate the catalyst system is greater than about 0.1 and less than about 2.5 moles per mole metal compound. In some embodiments of the invention, the amount of alcohol added to deactivate the catalyst system is greater than about 0.1 and less than about 2.0 moles per mole metal compound. In some embodiments of the invention, the amount of alcohol added to deactivate the catalyst system is greater than about 1.8 and less than about 2.2 moles per mole metal compound. In some embodiments of the invention, the amount of alcohol added to deactivate the catalyst system is greater than about 0.1 and less than about 2.2 moles per mole metal compound. In some embodiments, the metal compound is an alkylaluminum compound. In some embodiments, the number of moles of alcohol added to deactivate the catalyst system is based upon the number of moles of active metal alkyl units.

In other embodiments, the amount of alcohol added to deactivate the catalyst system is determined by the number of equivalents required to deactivate the catalyst. This equivalent ratio would be referred to as one equivalent of alcohol per equivalent of active metal alkyl unit. In yet other embodiments, the amount of alcohol added to deactivate the catalyst system may be greater than about 0.1 and less than about 1.8 equivalents per equivalent of active metal alkyl unit. In yet other embodiments, the amount of alcohol added to deactivate the catalyst system may be greater than about 0.1 and less than about 1.2 equivalents per equivalent of active metal alkyl unit. In yet other embodiments, the amount of alcohol added to deactivate the catalyst system may be greater than about 0.1 and less than about 1.0 equivalents per equivalent of active metal alkyl unit. In yet other embodiments, the amount of alcohol added to deactivate the catalyst system may be greater than about 0.1 and less than about 0.8 equivalents per equivalent of active metal alkyl unit. In yet other embodiments, the amount of alcohol added to deactivate the catalyst system may be greater than about 0.1 and less than about 0.5 equivalents per equivalent of active metal alkyl unit. In yet other embodiments, the amount of alcohol added to deactivate the catalyst system may be greater than about 0.6 and less than about 1.8 equivalents per equivalent of active metal alkyl unit. In yet other embodiments, the amount of alcohol added to deactivate the catalyst system may be greater than about 0.8 and less than about 1.2 equivalents per equivalent of active metal alkyl unit. In yet other embodiments, the amount of alcohol added to deactivate the catalyst system may be less than about 1.8 equivalents per equivalent of active metal alkyl unit. In yet other embodiments, the amount of alcohol added to deactivate the catalyst system may be less than about 1.2 equivalents per equivalent of active metal alkyl unit. In yet other embodiments, the amount of alcohol added to deactivate the catalyst system may be less than about 1.0 equivalents per equivalent of active metal alkyl unit. In yet other embodiments, the amount of alcohol added to deactivate the catalyst system may be less than about 0.8 equivalents per equivalent of active metal alkyl unit. In yet other embodiments, the amount of alcohol added to deactivate the catalyst system may be less than about 0.5 equivalents per equivalent of active metal alkyl unit. In some embodiments, the active metal alkyl unit is an alkylaluminum unit.

In some embodiments of the invention, the process to inhibit or limit the decomposition of a halide-containing olefin oligomerization catalyst system during recovery of an oligomerization product optionally includes the step of separating an intermediate stream into at least one product stream comprising olefin oligomerization product and at least one heavies stream.

In some embodiments of the invention, the olefin oligomerization catalyst system comprises a halogenated alkylaluminum or a mixture of a halogenated alkylaluminum and an alkylaluminum. In another embodiment of the invention, the olefin oligomerization catalyst system comprises a halide compound and a metal alkyl compound, such as an alkylaluminum compound.

In some embodiments of the invention, the alcohol has a boiling point different from the olefin product in the reactor effluent stream, e.g. does not form an azeotrope with the olefin product. In some embodiments of the invention, the alcohol is selected from the group of 1-hexanol, 3-hexanol, 2-ethyl-1-hexanol, 3-octanol, 1-heptanol, 2-heptanol, 3-heptanol, 4-heptanol, 2-methyl-3-heptanol, 1-octanol, 2-octanol, 4-octanol, 7-methyl-2-decanol, 1-decanol, 2-decanol, 3-decanol, 4-decanol, 5-decanol, 2-ethyl-1-decanol, and mixtures thereof.

In some embodiments of the invention, the alcohol is treated to minimize water content. In yet other embodiments of the invention, the water content of the alcohol is minimized before the formation of an intermediate stream.

In some embodiments of the invention, the separation of at least one olefin oligomerization product stream and at least one heavies stream is accomplished by distillation at a temperature less than or equal to about 200° C.

DESCRIPTION OF EMBODIMENTS OF THE INVENTION

While the invention will be described in connection with one or more embodiments, it will be understood that the invention is not limited to those embodiments. On the contrary, the invention includes all alternatives, modifications, and equivalents as may be included within the spirit and scope of the appended claims. The mention of or statement of a preference for certain embodiments does not indicate an intent to exclude other embodiments that are not mentioned or stated to be preferred.

The reaction contemplated here broadly relates to the oligomerization of ethylene and other lower olefins to produce higher olefins. In this context, "lower" and "higher" are relative; a lower olefin, as used in this disclosure is any 1-olefin that can be converted to a higher 1-olefin, wherein the higher 1-olefin has a greater number of carbon atoms than the lower olefin. The reaction is carried out in the presence of one or more catalysts under conditions encouraging the olefin oligomerization or polymerization to proceed. Moreover, it will be understood that the invention may also be used in connection with reactions to produce non-alpha olefins, such as polyalphaolefins and propylene tetramer.

The invention will be exemplified in the context of a trimerization reaction, although it is contemplated that the invention will find use in other olefin oligomerization reactions. "Trimerization," as used in this disclosure, is defined as any combination of three similar or dissimilar olefins reducing the number of olefin, i.e., carbon-carbon double bonds by two. For example, the three olefin bonds in the combination of three ethylene units can be reduced by two, to one olefin bond, in 1-hexene. In another example, the four olefin bonds in the combination of two 1,3-butadiene units can be reduced by two, to two olefin bonds, in 1,5-cyclooctadiene.

As used here, the term "trimerization" is also intended to include dimerization of diolefins, as well as "co-trimerization," each as further discussed below. The reactants, catalysts, equipment, and reaction conditions useful in the present process and the reaction products and co-products formed as a result of the trimerization reaction are further described below.

The reactants suitable for use in the trimerization process of this invention include olefinic compounds which can self-react, i.e., trimerize, to give useful products. For example, the self-reaction of ethylene can give 1-hexene, and the self-reaction of 1,3-butadiene can give 1,5-cyclooctadiene. Additionally, the trimerization process may include reaction of mixtures of olefinic compounds to give useful products such as, for example, trimerization of a mixture of ethylene and hexene can give mixtures comprising hexenes, decenes, tetradecenes and octadecenes, trimerization of mixtures of ethylene and 1-butene can give mixtures comprising hexenes, octenes, decenes, and dodecenes, trimerization of mixtures of 1-decene and ethylene can give mixtures comprising hexenes, tetradecenes, docosenes, and tricotene, and so on.

Olefins suitable for trimerization are those compounds having from about 2 to about 30 carbon atoms per molecule and having at least one olefinic double bond. Acyclic olefins are contemplated such as, for example, ethylene, propylene, 1-butene, 2-butene, isobutylene, 1-pentene, 2-pentene, 1-hexene, 2-hexene, 3-hexene, 1-heptene, 2-heptene, 3-heptene, the four normal octenes, the four normal nonenes, and mixtures of any two or more of those. Exemplary diolefin compounds contemplated here include, but are not limited to, 1,3-butadiene, 1,4-pentadiene, and 1,5-hexadiene.

If branched or cyclic olefins are used as reactants, while not wishing to be bound by theory, it is believed that steric hindrance could hinder the trimerization process. Therefore, reactants in which the branched or cyclic portion of the olefin are distant from the carbon-carbon double bond would be anticipated to yield more favorable results. The invention is not limited to use with the olefins suggested by this theory to be useful. Any olefin that will participate in the reaction is contemplated for use according to the invention.

Catalyst systems which may be used with this invention include any catalyst or co-catalyst which contains a halide such that may create hydrogen halides upon decomposition of the catalyst or deactivated catalyst system post-oligomerization reaction equipment. An example of one such catalyst system includes a chromium source, a pyrrole-containing compound and a metal alkyl, all of which have been optionally contacted and/or reacted in the presence of an unsaturated hydrocarbon. Optionally, these catalyst systems can be supported on an inorganic oxide support. These catalyst systems are especially useful for the dimerization and trimerization of olefins, such as, for example, ethylene to 1-hexene. For present purposes, any catalyst or catalyst system comprising a metal alkyl is more broadly contemplated. The catalyst system commonly includes a halide source, for example, a chloride, bromide, iodide, or fluoride compound. The terms "catalyst" and "catalyst system" may be used interchangeably herein and each term may be used to refer to either a single catalyst component or to a combination of multiple catalyst components.

The chromium source can be one or more organic or inorganic compounds, wherein the chromium oxidation state is from 0 to 6. Generally, the chromium source will have a formula of $CrX_n$, wherein X can be the same or different and can be any organic or inorganic radical, and n is an integer from 1 to 6. Exemplary organic radicals can have from about 1 to about 20 carbon atoms per radical, and are selected from the group consisting of alkyl, alkoxy, ester, ketone, and/or amido radicals. The organic radicals can be straight-chained or branched, cyclic or acyclic, aromatic or aliphatic, can be made of mixed aliphatic, aromatic, and/or cycloaliphatic groups. Exemplary inorganic radicals include, but are not limited to halides, sulfates, and/or oxides.

The chromium source may be a chromium(II)-containing and/or a chromium(III)-containing compound which can yield a catalyst system with improved oligomerization and/or trimerization activity. The chromium source may be a chromium(III) compound because of ease of use, availability, and enhanced catalyst system activity. Exemplary chromium(III) compounds include, but are not limited to, chromium carboxylates, chromium naphthenates, chromium halides, chromium pyrrolides, and/or chromium dionates. Specific exemplary chromium(III) compounds include, but are not limited to, chromium(III) 2,2,6,6,-tetramethylheptanedionate [Cr(TMHD)$_3$], chromium(III) 2-ethylhexanoate also called chromium(III) tris(2-ethylhexanoate) [Cr(EH)$_3$], chromium(III) naphthenate [Cr(Np)$_3$], chromium(III) chloride, chromic bromide, chromic fluoride, chromium(III) acetylacetonate, chromium(III) acetate, chromium(III) butyrate, chromium(III) neopentanoate, chromium(III) laurate, chromium(III) stearate, chromium(III) pyrrolides and/or chromium(III) oxalate.

Specific exemplary chromium(II) compounds include, but are not limited to, chromous bromide, chromous fluoride, chromous chloride, chromium(II) bis(2-ethylhexanoate), chromium(II) acetate, chromium(II) butyrate, chromium(II) neopentanoate, chromium(II) laurate, chromium(II) stearate, chromium(II) oxalate and/or chromium(II) pyrrolides.

The pyrrole-containing compound can be any pyrrole-containing compound that will react with the chromium source to form a chromium pyrrolide complex. As used in this disclosure, the term "pyrrole-containing compound" refers to hydrogen pyrrolide, i.e., pyrrole ($C_4H_5N$), derivatives of hydrogen pyrrolide, substituted pyrrolides, as well as metal pyrrolide complexes. A "pyrrolide", as used in this disclosure, is defined as a compound comprising a 5-membered, nitrogen-containing heterocycle, such as for example, pyrrole, derivatives of pyrrole, and mixtures thereof. Broadly, the pyrrole-containing compound can be pyrrole and/or any heteroleptic or homoleptic metal complex or salt, containing a pyrrolide radical, or ligand. The pyrrole-containing compound can be either affirmatively added to the olefin production reaction, or generated in-situ.

Generally, the pyrrole-containing compound will have from about 4 to about 20 carbon atoms per molecule. Exemplary pyrrolides include, but are not limited to, and may be selected from the group consisting of hydrogen pyrrolide (pyrrole), lithium pyrrolide, sodium pyrrolide, potassium pyrrolide, cesium pyrrolide, and/or the salts of substituted pyrrolides, because of high reactivity and activity with the other reactants. Examples of substituted pyrrolides include, but are not limited to, pyrrole-2-carboxylic acid, 2-acetylpyrrole, pyrrole-2-carboxaldehyde, tetrahydroindole, 2,5-dimethylpyrrole, 2,4-dimethyl-3-ethylpyrrole, 3-acetyl-2,4-dimethylpyrrole, ethyl-2,4-dimethyl-5-(ethoxycarbonyl)-3-pyrrolepropionate, ethyl-3,5-dimethyl-2-pyrrolecarboxylate, and mixtures thereof. When the pyrrole-containing compound contains chromium, the resultant chromium compound can be called a chromium pyrrolide.

Optionally, for ease of use, a chromium pyrrolide can provide both the chromium source and the pyrrole-containing compound. As used in this disclosure, when a chromium pyrrolide is used to form a catalyst system, a chromium pyrrolide can be considered to provide both the chromium source and the pyrrole-containing compound. While all pyrrole-containing compounds can produce catalyst systems with high activity and productivity, use of pyrrole and/or 2,5-dimethylpyrrole can produce a catalyst system with enhanced activity and selectivity to a desired product.

The metal alkyl can be any heteroleptic or homoleptic metal alkyl compound. One or more metal alkyls can be used. The alkyl ligand(s) of the metal alkyl can be any aliphatic and/or aromatic radical. Preferably, the alkyl ligand(s) are any saturated or unsaturated aliphatic radical. The metal alkyl can have any number of carbon atoms per molecule. However, due to commercial availability and ease of use, the metal alkyl usually will comprise less than about 70 carbon atoms per metal alkyl molecule and preferably less than about 20 carbon atoms per molecule. Exemplary metal alkyl compounds include, but are not limited to, alkylaluminum compounds, alkylboron compounds, alkylmagnesium compounds, alkylzinc compounds and/or allyl lithium compounds. Examples of metal alkyl compounds include, but are not limited to, n-butyl lithium, sec-butyllithium, tert-butyllithium, diethylmagnesium, diethylzinc, triethylaluminum, trimethylaluminum, triisobutylaluminum, and mixtures thereof.

The metal alkyl may be selected from the group consisting of non-hydrolyzed, i.e., not pre-contacted with water, alkylaluminum compounds, derivatives of alkylaluminum compounds, halogenated alkylaluminum compounds, and mixtures thereof for improved product selectivity, as well as improved catalyst system reactivity, activity, and/or productivity. The use of hydrolyzed metal alkyls can result in decreased selectivity to the desired olefin trimerization product and increased co-product formation, such as heavies.

The metal alkyl may be a non-hydrolyzed alkylaluminum compound, expressed by the general formulae $AlR_3$, $AlR_2X$, $AlRX_2$, $AlR_2(OR)$, $AlRX(OR)$, and/or $Al_2R_3X_3$, wherein R is an alkyl group, X is a halogen atom, and wherein if the formula contains more than one R group, such R groups may be either the same alkyl group or different alkyl groups and independent of each other. Exemplary compounds include, but are not limited to, triethylaluminum, tripropylaluminum, tributylaluminum, diethylaluminum chloride, diethylaluminum bromide, diethylaluminum ethoxide, diethylaluminum phenoxide, ethylaluminum dichloride, ethylaluminum sesquichloride, and mixtures thereof for best catalyst system activity and product selectivity. In one aspect of the invention, triethylaluminum (TEA) and diethylaluminum chloride (DEAC) are used. In one aspect of the invention, the oligomerization catalyst comprises a halogenated alkylaluminum compound, which may be expressed by the general formulae $AlR_2X$, $AlRX_2$, $AlRX(OR)$, and/or $Al_2R_3X_3$, wherein R is an alkyl group, X is a halogen atom, and wherein if the formula contains more than one R group, such R groups may be either the same alkyl group or different alkyl groups and independent of each other. Exemplary halogenated alkylaluminum compounds include diethylaluminum chloride, diethylaluminum bromide, ethylaluminum dichloride, ethylaluminum sesquichloride, and mixtures thereof.

While not wishing to be bound by theory, it is believed that a chloride containing-compound can improve product purity and selectivity. Any chloride-containing compound can be used, such as, for example, DEAC and/or organochlorides. Exemplary organochlorides include, but are not limited to, carbon tetrachloride, methylene chloride, chloroform, benzylchloride, hexachloroethane and mixtures thereof.

One composite catalyst which may be used in the invention is the combination of chromium (III) ethylhexanoate, 2,5-dimethylpyrrole, triethylaluminum, and diethylaluminum chloride. This composite catalyst system can be used, for example, to trimerize ethylene, forming 1-hexene.

Usually, contacting and/or reacting the chromium source, pyrrole-containing compound and metal alkyl is done in the presence of an unsaturated hydrocarbon. The unsaturated hydrocarbon can be any aromatic or aliphatic hydrocarbon, in a gas, liquid or solid state. To effect thorough contacting of the chromium source, pyrrole-containing compound, and metal alkyl, the unsaturated hydrocarbon may be in a liquid state. It will be understood, however, that the invention may be used in connection with appropriate catalyst systems, irrespective of the method of producing the catalyst system.

The unsaturated hydrocarbon can have any number of carbon atoms per molecule. Usually, the unsaturated hydrocarbon will comprise less than about 70 carbon atoms per molecule, or less than about 20 carbon atoms per molecule. Exemplary unsaturated, aliphatic hydrocarbon compounds include, but are not limited to, ethylene, 1-hexene, 1,3-butadiene, and mixtures thereof. In one aspect of the invention, the unsaturated aliphatic hydrocarbon compound is 1-hexene. Exemplary aromatic hydrocarbons include, but are not limited to, benzene, toluene, ethylbenzene, xylene, mesitylene, hexamethylbenzene, and mixtures thereof. Unsaturated, aromatic hydrocarbons may be used to improve catalyst system stability, as well as produce a highly active and selective catalyst system.

It should be recognized, however, that the reaction mixture comprising a chromium source, pyrrole-containing compound, metal alkyl and unsaturated hydrocarbon can contain additional components which do not adversely affect and can enhance the resultant catalyst system, such as, for example, transitions metals and/or halides.

The oligomerization reaction products, i.e., olefin trimers, can be prepared from the catalyst system of this invention by solution, slurry, and/or gas phase reaction techniques using conventional equipment and contacting processes. Contacting of the monomer or monomers with a catalyst system can be effected by any manner known in the art. One convenient method is to suspend the catalyst system in an organic medium and to agitate the mixture to maintain the catalyst system in solution throughout the trimerization process. Other known contacting methods can also be employed.

For example, a continuous-feed autoclave reactor with a fluid jacket or internal heat transfer coil and any suitable stirring mechanism, such as, for example, mechanical stirring or the sparging with an inert gas, typically nitrogen, may be used. In another embodiment, a loop reactor with mechanical stirring, such as, for example, a circulating pump, can be used. Alternatively, tubular reactions for carrying out the oligomerization may also be used in connection with the invention.

Alternatively, the trimerization process can be carried out in a slurry of the catalyst components in an inert medium or diluent which is the process medium. Broadly, the common diluents are fluid paraffins, cycloparaffins, or aromatic hydrocarbons. Exemplary reactor diluents include, but are not limited to, isobutane, cyclohexane, and methylcyclohexane. Isobutane can be used for enhanced compatibility with known olefin polymerization processes. However, a homogenous trimerization catalyst system is more easily dispersed in cyclohexane. In one embodiment, a homogeneous catalyzed trimerization process is carried out in cyclohexane.

In accordance with another embodiment of this invention, a slurry process can be carried out in a diluent (medium), which is a product of the olefin oligomerization process. Therefore, the choice of reactor diluent, or medium, is based on the selection of the initial olefin reactant. For example, if the oligomerization catalyst is used to trimerize ethylene to 1-hexene, the solvent for the oligomerization reaction would be 1-hexene. If ethylene and hexene were trimerized to produce decene, the oligomerization reaction solvent would be 1-hexene. If 1,3-butadiene was trimerized to 1,5-cyclooctadiene, the trimerization reactor solvent would be 1,3-butadiene or 1,5-cyclooctadiene, and so on.

Reaction temperatures and pressures can be any temperature and pressure which are suitable to trimerize the olefin reactants using said catalyst system. Generally, reaction temperatures are within a range of about −20° to about 250° C. In another aspect of the invention, reaction temperatures are within a range of about 60° to about 200° C. In yet another aspect, reaction temperatures are within a range of 80° to 150° C. Generally, reaction pressures are within a range of about atmospheric to about 2500 psig. In another aspect of the invention, reaction pressures may be within a range of about atmospheric to about 1000 psig. In yet another aspect of the invention, the reaction pressure ranges between about 300 and about 900 psig.

When the reactant is predominately ethylene, a temperature in the range of about 0° to about 300° C. generally can be used. In another aspect of the invention, when the reactant is predominately ethylene, a temperature in the range of about 60° to about 130° C. is employed.

Too low of a reaction temperature can produce too much undesirable insoluble product, such as, for example, polymer, and too high of a temperature can cause deactivation of the catalyst system and isomerization of the reaction products. Too low of a reaction pressure can result in low catalyst system activity.

Optionally, hydrogen can be added to the reactor to accelerate the reaction and/or increase catalyst system activity. If desired, hydrogen also can be added to the reactor to suppress polymer production.

The contents of the reactor can be agitated or stirred by an inert gas (e.g. nitrogen) purge, by introducing the reactant, hydrogen, fluid medium, or catalyst or exhausting the effluent in a manner causing agitation, by mechanical or magnetic stirring, or in any other suitable manner.

The reaction usually is run continuously by steadily charging lower 1-olefin reactant(s), catalyst system, and process medium and removing the liquid contents of the reactor. For example, a continuous stirred tank reactor system can be employed that includes feed systems for catalyst system, reactant and medium and a discharge system for the effluent. Alternatively, a batch process can also be employed.

The trimerization reaction is exothermic, so the reaction temperature usually can be regulated by circulating cooling water through a jacket or heat transfer coil, thus transferring heat out of the reactor. It is important to be able to transfer heat efficiently out of the reactor, so the reactor can be effectively maintained at the desired reaction temperature. Another advantage of more effective heat transfer is that the trimerization reaction can be run at a higher throughput for a given temperature, which can improve production efficiency.

The reactor effluent is treated to deactivate the active catalyst, and may further be treated to separate products, recycle the residual reactants, medium, and other components suitable for recycling, and dispose of any components that are not recycled.

When the oligomerization or trimerization process is deemed to be complete, the reactor effluent stream comprising solvent, olefin product(s), catalyst system, and some polymer and/or oligomer, is contacted with an alcohol. Any alcohol which is soluble in the reactor effluent stream can be used. As used herein, the term "alcohol" includes monoalcohols, diols, and polyols. An alcohol is selected that has a boiling point, or molecular weight, such that the alcohol will not azeotrope with the olefin monomer product. In some embodiments of the invention, the alcohol has a boiling point different from the olefin product in the reactor effluent stream. In an exemplary process, wherein the catalyst system is used to trimerize ethylene to 1-hexene, an alcohol with six or more carbon atoms per molecule may be used. Alternatively, an alcohol having six to twelve carbon atoms per molecule may be used for catalyst system deactivation. Such alcohols are easily removable from the 1-hexene olefin product. Exemplary alcohols include, but, are not limited, 1-hexanol, 2-hexanol, 3-hexanol, 2-ethyl-1-hexanol, 1-heptanol, 2-heptanol, 3-heptanol, 4-heptanol, 2-methyl-3-heptanol, 1-octanol, 2-octanol, 3-octanol, 4-octanol, 7-methyl-2-decanol, 1-decanol, 2-decanol, 3-decanol, 4-decanol, 5-decanol, 2-ethyl-1-decanol, and mixtures thereof.

Alternatively, a low-molecular-weight diol or polyol, for example ethylene glycol, can be used as a catalyst deactivation agent. Diols and polyols commonly have much higher boiling points than monoalcohols of comparable molecular weight, and thus can be separated more easily from 1-hexene.

The alcohol is added to the reactor effluent stream in an amount sufficient to quench or kill, either of which deactivate, the olefin production catalyst system and to inhibit, or halt: (1) production of undesirable solids, i.e., polymer; and/or (2) product purity degradation due to isomerization, in the product separation process. However, it has been found that addition of excess deactivation agent increases potential for corrosion in process components downstream of the deactivation agent addition point. It has further been found that use of specific ranges of ratio of moles of deactivation agent to moles of aluminum significantly decreases the amount of hydrogen halide acid formed from the decomposition of the aluminum halide alkoxide. Thus, in one aspect of the invention, the catalyst deactivation stage is carried out using a mole ratio of deactivation agent to aluminum of between about 1.5 and about 2.5. It will be understood, however, that such mole ratio may be more generally described as a ratio of moles deactivation agent to moles metal. Table 6 illustrates the effect of this mole ratio on the formation of hydrogen chloride. For the example illustrated in Table 6, the alkyl aluminum was diethylaluminum chloride and the alcohol was 2-ethyl-1-hexanol.

After the catalyst has been deactivated, olefin product(s), such as, for example, 1-hexene, can be removed. Any removal process can be used, including for example, distillation.

Figure 1:
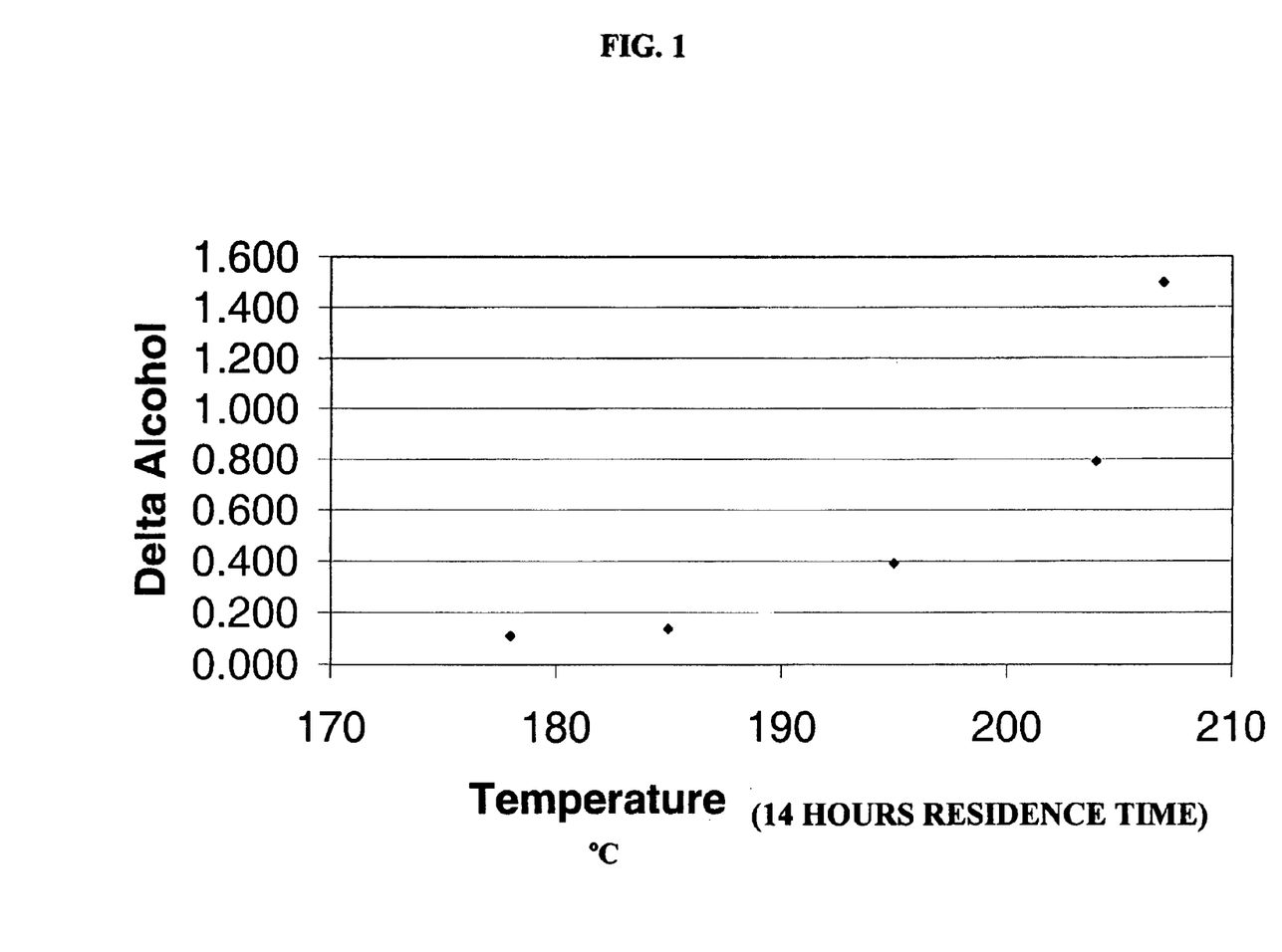
FIG. 1 illustrates the effect of temperature on decomposition of the aluminum alkoxide resulting from catalyst deactivation (the "aluminum alkoxide") for a mixture in which 2.0 equivalents of alcohol is used to deactivate the oligomerization catalyst.
Figure 2:
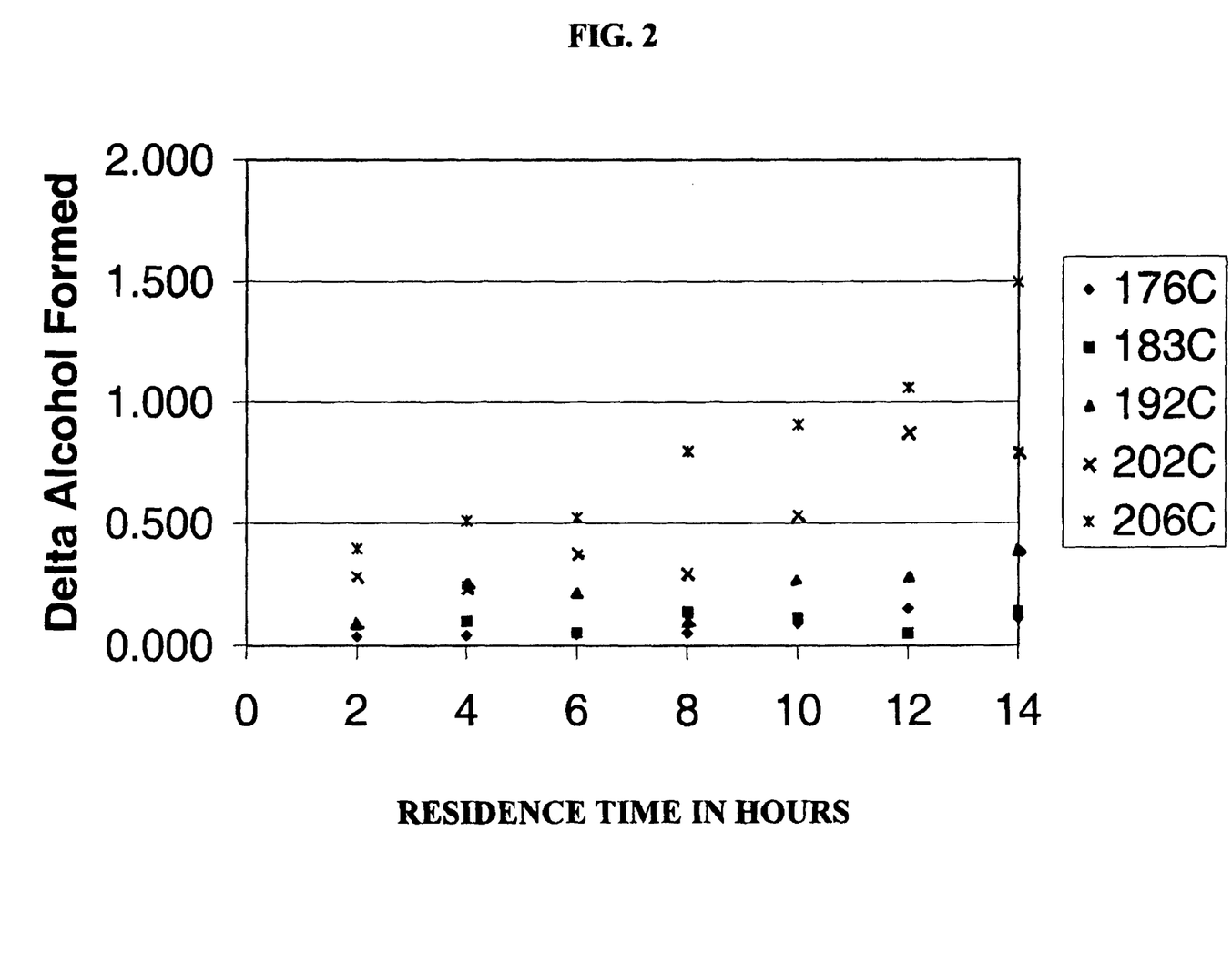
FIG. 2 illustrates the effect of residence time, at a number of different temperatures, on decomposition of the aluminum alkoxide for a mixture in which 2.0 equivalents of alcohol is used to deactivate the oligomerization catalyst.

In a simple distillation separation scheme, unreacted olefin, i.e. ethylene, is removed from the reaction product first, i.e. olefin trimer or 1-hexene, then the reaction product is removed, and finally, the medium is distilled away from the remaining deactivated catalyst and co-products such as heavies. Maintaining relatively low temperatures and short residence times in the separation stage of the process decreases the formation of the acid gasses and other undesirable decomposition residues and thereby prevents or inhibits downstream process equipment corrosion. In one aspect of the invention, the distillation column bottoms or reboiler temperatures are maintained below about 200° C. In another aspect of the invention, distillation column bottoms or reboiler temperatures are maintained below about 190° C. In yet another aspect of the invention, the distillation column bottoms or reboiler temperature is below about 175° C. FIGS. 1 and 2 indirectly illustrate the effect of temperature on the potential for corrosion downstream due to the deactivated catalyst decomposition as measured by the increase in the alcohol formation shown parallels an increase in hydrogen halide acid formation. An increase in hydrogen halide acid concentration directly affects the potential for corrosion in downstream processing equipment.

Figure 4:
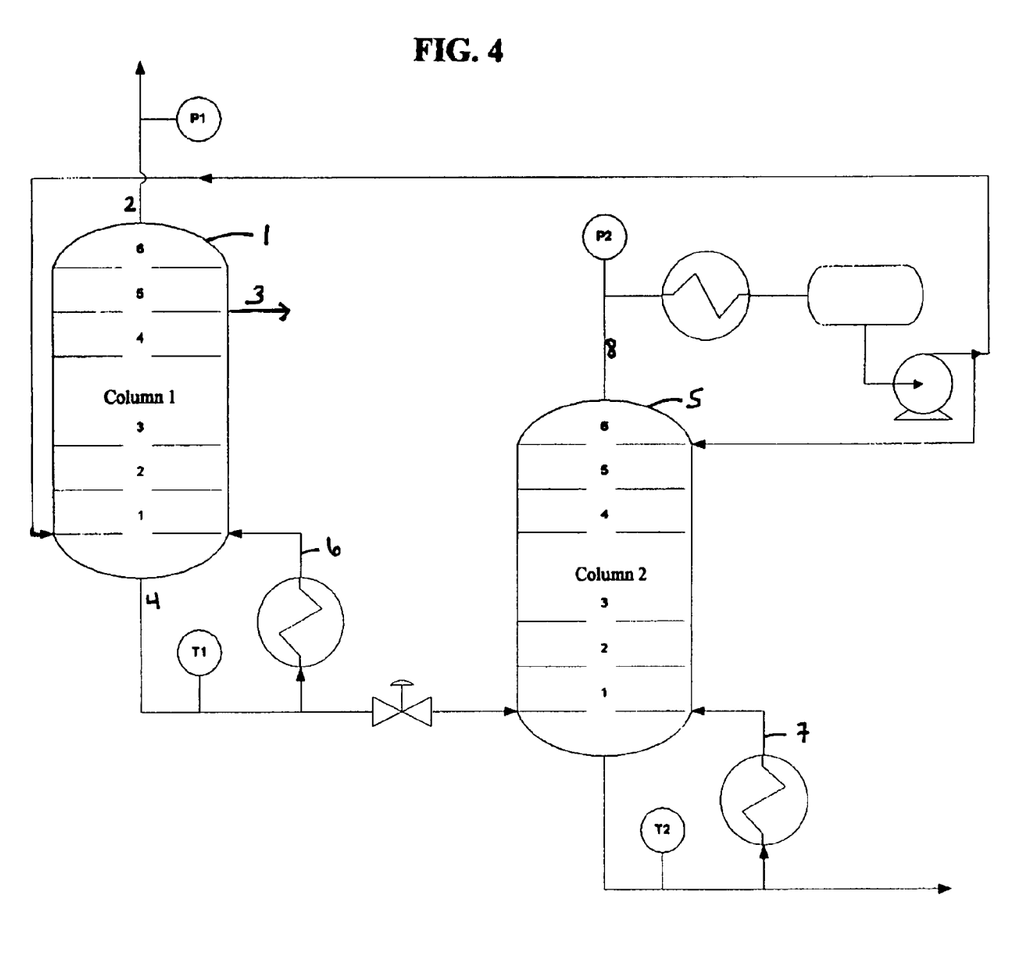
FIG. 4 is a schematic of a product separation scheme useful in one embodiment of the invention.

In order to maintain the lower temperatures indicated above and yet effectively separate the unreacted olefin, the olefin trimer and deactivated catalyst and derivatives thereof and co-products, a two stage distillation unit may be utilized. FIG. 4 depicts such a distillation scheme. The reactor effluent into which the alcohol has been previously added is injected into a first column 1. An unreacted olefin stream is removed overhead at 2, a middle distillate stream containing primarily olefin trimer and reaction medium is removed at 3 and a bottoms stream containing deactivated catalyst components and polymer co-products is removed at 4. The bottoms of first column 1 are fed into a second column 5. As shown in FIG. 4 at 6 and 7, respectively, column 1 and column 5 may each be reboiled. An overhead stream 8 from second column 5 is recycled back into first column 1. The operating pressure of first column 1 is set such that the operating temperature of first column 1 is below about 200° C. while yet effecting separation of the overhead, middle distillate and bottoms streams. The operating pressure of second column 5 is less than the operating pressure of first column 1 so as to permit recovery of the reaction medium while maintaining separation temperatures of no more than about 200° C. in both first and second columns 1 and 5. In some embodiments, the overall residence time of the deactivated catalyst at the high temperatures necessary for the separation is minimized. In some embodiments of the invention, first column 1 is large by comparison to second column 5 such that the bottoms stream from first column 1 is significantly higher than the bottoms (or bottoms and side) stream from second column 5. Thus, this combination of columns 1 and 5 significantly reduces the residence time of heavy components in the combined separation.

The separation scheme illustrated in FIG. 4 and discussed above is intended to exemplify one separation method and is not intended to limit the distillation schemes useful in the invention. Alternative distillation schemes which effect the separation of the unreacted olefin, olefin trimer and the concentrated dispersion containing co-product polymer and catalyst components while maintaining bottoms or reboiler temperatures of no more than about 200° C., about 190° C. or about 175° C. are within the invention. For example, in an alternative embodiment of the invention, no middle distillate stream 3 is recovered from first column 1, only unreacted olefin is removed overhead, and the olefin trimer product plus reaction medium is sent with the bottoms stream to the second column. Alternatively, the reactor effluent may first be sent to a pressure letdown vessel from which some or all of the lower olefin may be removed. It will be apparent to one of ordinary skill in the art that a large number of such variations may be made to the separation scheme while remaining within the scope of the invention.

Figure 3:
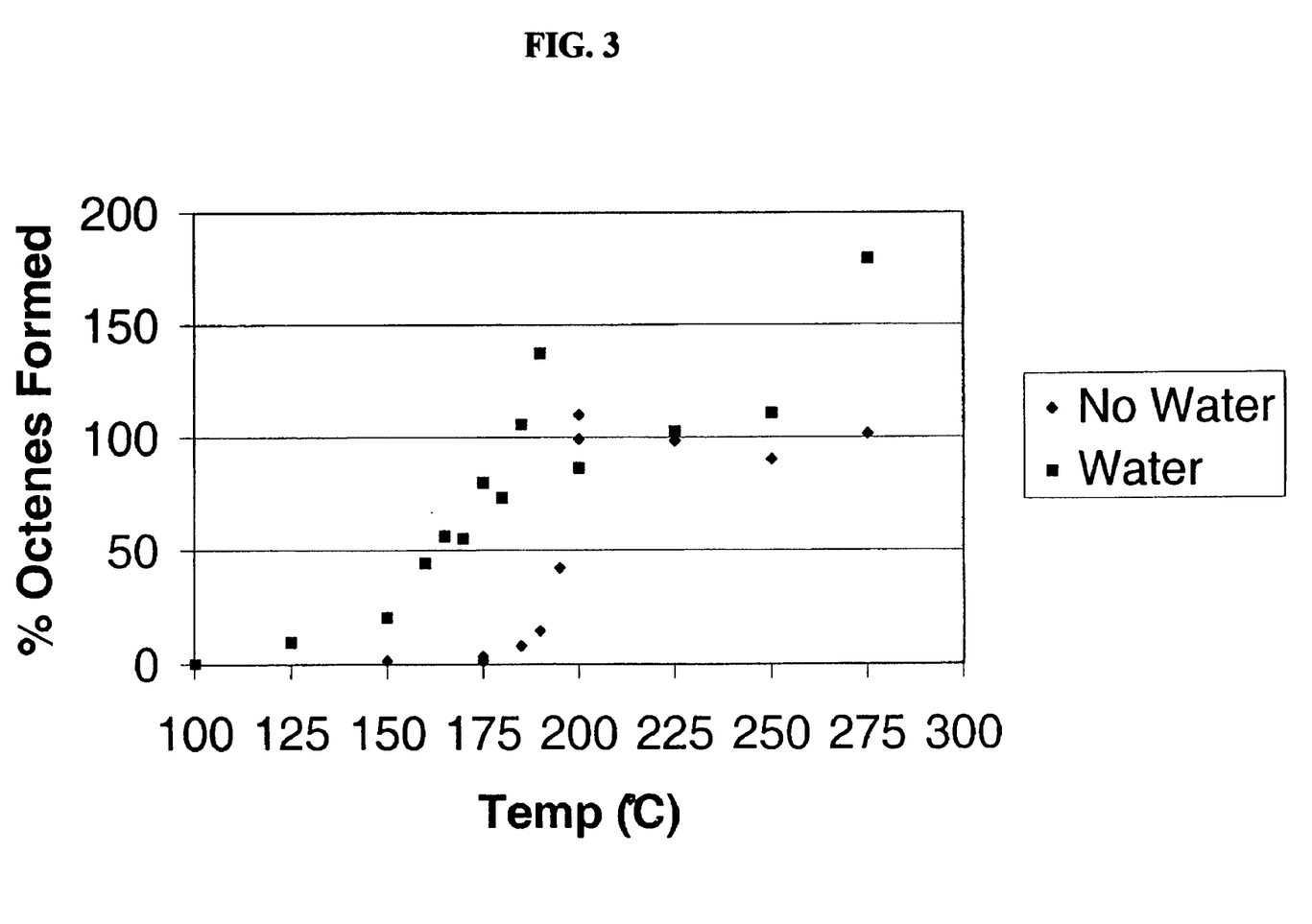
FIG. 3 illustrates the effect of water in the catalyst deactivation agent on the temperature at which octenes are formed as a result of the aluminum alkoxide decomposition.

During deactivation of the active catalyst with an alcohol, mixtures of aluminum halide alkoxides and other compounds are formed. It has been discovered that the presence of water in the alcohol used as a catalyst deactivation agent facilitates the formation of hydrogen halides by aluminum halide alkoxide decomposition. FIG. 3 illustrates this water effect on the formation of hydrogen halides; in FIG. 3, the formation of hydrogen halides is represented as the formation of octenes since a parallel decomposition of the deactivated catalyst derivative by dehydration is to form octenes. As can be seen in FIG. 3, the presence of water in the deactivation agent lowers the temperature at which the hydrogen halides are formed. Therefore, in another aspect of the invention, the deactivation agent is dried before being introduced into the reactor effluent.

Numerous processes for removing or minimizing the water in alcohols, such as ternary azeotrope distillation and use of adsorbents, are well known. Known adsorbents include, for example, alumina, clinoptilolite, zeolite, molecular sieves, sodium-A, bauxite, fuller's earth and acid-activated bentonite. Ternary azeotrope distillation involves addition to a water-alcohol azeotrope, a third component which is soluble in water but not alcohol. The ternary solution is then distilled. Suitable third components include, for example, diisopropyl ether, ethyl ether, pentane and cyclohexane. Any of the known methods, or combinations thereof, may be used in removing or minimizing the water in the alcohol deactivation agent which may be used in the invention.

The concentrated dispersion containing co-products and deactivated catalyst may be discarded, or can be further treated as described below.

The product stream produced by the ethylene trimerization process commonly contains one or more of the following compounds butene; 1-hexene; internal hexenes (i.e. 2-hexene or 3-hexene); octenes; decenes; reaction medium; and "heavies."

The stream formed by removing the desired olefin monomer products can be further processed by contacting it with an aqueous inorganic base to remove metals. Such process may be accomplished by adding an aqueous, inorganic base to the heavies stream which remains after at least one product stream comprising at least one olefin oligomerization product is separated from an intermediate stream which is formed by contacting an olefin oligomerization reactor effluent stream with an alcohol. The addition of the aqueous inorganic base to the heavies stream forms an aqueous phase which comprises the inorganic base; an organic phase which comprises olefin product(s), polymer(s) and/or oligomer(s); and a precipitate which comprises chromium. The precipitate may be removed from the aqueous phase and organic phase, the aqueous phase and organic phase separated; and a mineral acid selected from the group consisting of sulfuric acid, phosphoric acid and mixtures thereof added to the aqueous phase to remove substantially all of the aluminum. The organic layer may be disposed of. Suitable aqueous inorganic bases include, for example, sodium hydroxide, potassium hydroxide, and mixtures thereof. An exemplary mineral acid is sulfuric acid.

The trimerization process commonly produces two residues that can build up on the internal surfaces of the reactor. One residue, long recognized to build up on the walls of the reactor, is an oligomer or a polymer having a chain length higher than the intended product, formed as a co-product. This higher oligomer or polymer residue is referred to here as "polymer residue." For example, in the case of an ethylene reaction, polyethylene can be formed and build up on the internal surfaces of the reactor. This polymer residue can detract from the heat transfer efficiency of the internal surfaces of the reactor.

Polymer residue can be removed from a trimerization reactor by washing the reactor with a solvent for the residue. The trimerization reactor commonly is supplied with a solvent for co-product polymers, such as, for example, cyclohexane or methylcyclohexane, as the process medium. When a polymer solvent is used as the process medium, the same process medium can be used to periodically flush out the reactor. The washing conditions can be more stringent than the usual process conditions, in order to remove the polymer residue that is not removed under the usual process conditions. For example, the washing step can be a "hot wash," carried out by circulating the usual process medium at a higher temperature than the process temperature to melt, more quickly dissolve, or otherwise dislodge polymer residue.

In a continuous ethylene trimerization process, the hot wash can be carried out as follows. The reaction can be halted by stopping the feed of catalyst system and reactants while continuing to inject and drain the reactor medium, i.e. cyclohexane or methylcyclohexane, and increasing the medium temperature by 60° C. to 70° C. The hot wash can be continued for several hours, or as long as necessary to remove all or substantially all polymer residue. This hot wash has been found to remove the buildup of polymer residue.

A second residue, which the present inventors have found also can detract substantially from the heat transfer efficiency of the reactor, is referred to here as catalyst residue. The inventors have not determined the exact chemical composition of this catalyst residue. It can be a precipitate or deposit of the entire catalyst system or one or more of the catalyst system components, the product of a reaction between the catalyst system components, the catalyst system and the reactor wall, deactivated catalyst system constituents, a combination of these residues, or something else. The residue is believed to be associated with the catalyst system, though the present invention is not limited by the accuracy of that theory.

One material useful for breaking down and allowing the removal of this catalyst residue is an alcohol. Suitable alcohols for this purpose include the catalyst deactivation agent alcohols, as described above. As with the catalyst deactivation agent alcohols, it is useful here to employ an alcohol that is easily separable from (for example, does not form an azeotrope with) the trimerization product and other reaction constituents.

The alcohol can be introduced to contact the catalyst residue on the interior surfaces of the reactor in a variety of ways.

As one example, the alcohol can be added to the process medium during the hot wash, thus removing the polymer and catalyst residues together. A convenient proportion of the alcohol in the process medium is from about 0.01 ppm (mg/kg) to about 10% by weight, alternatively, from about 0.01 ppm to about 1% by weight, or alternatively, from about 1 ppm to about 3000 ppm.

After the hot wash is carried out in a continuous reactor as described previously, the reactor can be returned to service by: (1) stopping the feed of alcohol, (2) continuing the feed of the process medium until the effluent temperature returns to the working process temperature (thus flushing the alcohol out of the reactor), (3) resuming the feed of the catalyst until its concentration is adequate to resume the reaction, then (4) resuming the reactant feed and thus restarting the reaction.

As another example, an alcohol can be added to the charge in the reactor at the end of a batch process, or just before a continuous process is shut down, to prevent or remove the buildup of catalyst residue on the interior surfaces of the reactor. As used in this disclosure, "prevention" or "removal" of catalyst residue are both referred to as "removal," for ease of use. Thus, "removal" means either preventing catalyst residue from forming or removing already-formed catalyst residue. In this example, the temperature of the reactor can be increased to improve the removal of both the polymer and the catalyst residues at the same time.

The alcohol added to the reactor to clean out catalyst residue can also partially or completely deactivate the catalyst in the remaining charge of reactor contents. Thus, the alcohol feed into the effluent to deactivate the catalyst during continuous operation may be moderated or discontinued during the reactor cleaning process sequence.

In one contemplated embodiment, a continuous trimerization process can be shut down every few weeks and the reactor hot washed, which in this embodiment may require 6-9 hours. More frequent or less frequent hot wash treatments may also be employed, within the scope of the invention.

In another embodiment, a more frequent, much shorter hot wash can be introduced into the production cycle to reduce or eliminate the need for the conventional, long-duration hot wash carried out every few weeks. Longer periods of operation between shutdowns can thus be scheduled, which may prove more efficient.

It may also prove useful to hot wash the reactor conventionally and hot wash it with a medium containing alcohol on different schedules. For example, if the catalyst residue builds up more slowly than the polymer residue, the reactor can be hot washed more frequently than it is washed with an alcohol additive.

In any case disclosed above, the alcohol can be removed from the reactor effluent by distillation, just as the catalyst deactivation agent is conventionally removed from the reactor effluent. Optionally, the washing effluent can be passed through the same distillation apparatus used for isolating the trimerized reaction product. Using this effluent treatment, minimal changes to the process are required to allow removal of residues from the interior surfaces of the reactor.

EXAMPLES AND COMPARATIVE EXAMPLES

The apparatus used for all runs discussed below was a one liter three necked roundbottom flask equipped with a glass well for a thermocouple to monitor the kettle temperature, an addition funnel, a magnetic stirrer and a Dean-Stark tube that allowed overhead to be constantly returned to the kettle or removed for sampling. A condenser was placed at the top of the Dean-Stark tube as was a thermocouple. A pH strip was held at the top of the Dean-Stark tube. The flask was also equipped with a magnetic stirring bar with a stirrer and a heating mantle. A nitrogen stream constantly swept material through a bubbler containing 0.1N NaOH.

In a typical experiment 200 g dodecane was added to the flask and the system purged with nitrogen. Selective 1-hexene catalyst, e.g. ethylene trimerization catalyst system, was then charged to the flask from a metal cylinder. The desired amount of 2-ethylhexanol was then added slowly and allowed to react. The temperature rose to approximately 80° C. and gas evolution was observed. The contents were stirred for 30 minutes to allow complete reaction and the kettle sampled. Decane (50 mL) was added and the contents heated to reflux. Overhead was removed to obtain the desired kettle temperature. The overhead was sampled (about 2 mL) every two hours and a typical run was 2 days or 14 hours residence time. The kettle was also sampled at the beginning of the second day (for a two day run) and at the end of the run. The base bath was titrated with 0.1N $H_2SO_4$ to determine the amount of acid generated by the experiment. In other experiments, diethylaluminum chloride, DEAC, (about 30 g) was dissolved in ethylbenzene (about 145 mL) and used in place of the 1-hexene catalyst.

Thermal tests of the alcohol deactivated 1-hexene catalyst were undertaken in greater detail than that mentioned above. This was necessary to determine more exactly the temperature and time stability of the deactivated catalyst to provide additional and more accurate information for the recommended operating conditions of a plant. The stability of the deactivated 1-hexene catalyst was judged by the formation or disappearance of the pyrrole component or the formation of the alcohol deactivation agent used to form the alkoxide or alkoxide decomposition products such as octenes. All of the amounts were delta percents formed in the overhead.

This series of experiments was made using three levels of 2-ethylhexanol added to a standard 1-hexene catalyst. The levels of alcohol added were 1.8 moles alcohol/moles metal, 2.0 moles alcohol/moles metal and 2.2 moles alcohol/moles metal. The metal was considered to be the combined moles of chromium and aluminum present in the catalyst. Experiments were run at different temperatures with each alcohol level. Since the temperature of the kettle was controlled by the amount of overhead removed, the results were compared by using the delta amount of the product formed. The delta amount was obtained by using the first overhead sample as a starting or zero point and the delta amount listed is the difference between the amount at the starting point and at the time point being analyzed. Typically the experiments were run for 14 hours in the apparatus described in the experimental section. Overhead samples were taken every two hours and analyzed by GC. The base bubbler was titrated at the end of each experiment but frequently insufficient acid gas was formed to be detected by titration.

The assessment of temperature sensitivity was done by examining the 14 hours on stream sample for deactivated catalyst decomposition by the formation of octenes, the presence of alcohol and the appearance or disappearance of 2,5-dimethylpyrrole at different temperatures. The decomposition temperature was observed to occur just above 190° C. (374° F.) at all of the alcohol deactivation levels. It is of interest to note that the pyrrole levels increased when 1.8 moles of alcohol is used but decreased with 2.0 and 2.2 moles of alcohol/moles of metal.

In addition to the temperature effect of the deactivated catalyst decomposition, it was important to know the effect of time on the deactivated catalyst decomposition process. Information on this effect was obtained by running each alcohol level at different temperatures and monitoring the reaction every two hours. While there is some scatter in the data, there appears to be very little deactivated catalyst decomposition at 2 hours on stream below 190° C. (374° F.) at all of the alcohol levels. Deactivated catalyst decomposition is observed to increase with both hours on stream and temperature. The deactivated catalyst decomposition is again assessed by the formation of octenes and alcohol and by the disappearance of 2,5-dimethylpyrrole. Pyrrole is known to oligomerize in the presence of acid and may serve as a protective influence during the decomposition of the deactivated catalyst by the consumption of the acid gas formed. Thus, it is desirable to run at as low a temperature as practical with as short a residence time as practical.

It is also noted that the formation of octenes and alcohol is dramatically increased when 2.2 moles of alcohol/mole metal is used. There is also a much larger decrease in the amount of pyrrole at 2.2 moles of alcohol/moles metal compared to using 2.0 moles of alcohol/moles of metal. The overall data illustrates that excess alcohol increases the rate of deactivated catalyst decomposition. Even under these high alcohol levels the amount of deactivated catalyst decomposition is very small or non-existent at 2 hours on stream below 190° C. The effect of excess alcohol on pure DEAC is very prominent and will be discussed later and compared to excess alcohol with the standard catalyst.

It was noted that at 1.8 moles alcohol/moles metal, that alcohol formation does not occur until the highest temperature (200° C.) and then not until 10 hours on stream. From titration experiments, it appears that not all the alkyl aluminum has been reacted so that when alcohol which may be produced by deactivated catalyst decomposition reacts with the remaining alkyl aluminum and is therefore bonded to the aluminum and not seen in the overhead.

The deactivated catalyst concentration used in these experiments is much more concentrated in order to see the effects of the experimental variables.

Effect of Water on Deactivated Catalyst Decomposition

In order to assess the effect of water on the decomposition of the alcohol deactivated catalyst, several runs were made with water added to the deactivated catalyst mixture. The effects of both the amount of water and temperature are shown in Table 5.

TABLE 5

Water Addition and Temperature Effect

| Water Added (g) | 0.62 | 1.99 | 2.00 | 2.00 | 2.00 | 4.52 |
|---|---|---|---|---|---|---|
| Moles Alcohol/Moles Metal | 2.0 | 1.8 | 2.0 | 2.0 | 2.0 | 2.0 |
| Hours on Stream | 14 | 14 | 14 | 14 | 14 | 1.5 |
| Average Kettle Temp (C.) | 191 | 173 | 189 | 198 | 203 | 204 |
| % Total Octenes | 0.465 | 0.983 | 3.943 | 6.894 | 18.681 | 21.49 |
| Delta % 2,5-Dimethylpyrrole | −0.216 | 0 | −1.571 | −0.266 | −0.344 | 2.103 |
| % 2-Ethylhexanol | 2.194 | 2.309 | 4.571 | 10.633 | 14.465 | 5.465 |
| % Decomposition to HCl | 0.16 | 0.28 | 0.3 | 0.21 | — | 1.5 |

As the amount of water is increased, it is noticed that the total percent octenes increases as does the total percent of alcohol. Increasing the temperature, at constant water levels (2.0 g), also increases the formation of both of these compounds. The delta amount of pyrrole generally is reduced but the data are not very consistent. Until the largest amount of water was added (4.52 g), it was not really possible to determine the percent decomposition to HCl by titration of the bubbler. It was, however, possible to see a slight change in the color of the pH paper as the temperature was raised from 189° C. to 203° C. It should be noted that the run with the largest amount of water added was only on stream for 1.5 hours as solids formed and it was not possible to stir the mixture. However, sufficient acid was formed to be detectable by titration of the base bubbler. Both water amount and temperature have an effect on the decomposition path to HCl. It would appear that monitoring the amounts of octenes, alcohol and pyrrole in the mixed decene stream would give an early warning that the operating conditions that may cause decomposition of deactivated catalyst to HCl and subsequent corrosions are being approached. The effect of water on pure DEAC is discussed under the heading of "Pure Components."

Pure Components

After tests of the alcohol deactivated 1-hexene catalyst were undertaken to determine the temperature and time stability in order to provide information for the recommended operating conditions. It appeared that additional understanding of the decomposition of the aluminum alkoxides would be of value in confirming the information obtained using the 1-hexene catalyst mixtures. Several experiments were undertaken using the alkoxides formed from pure DEAC and/or TEA by the addition of 2-ethylhexanol. These compounds were tested in the same solvent system employed for the 1-hexene catalyst. The results of these experiments will be described.

Amount of Alcohol Effect

The decomposition of the deactivated 1-hexene catalyst appeared to increase when excess alcohol was used. It was decided to investigate this effect with the aluminum alkoxide formed from DEAC and 2-ethylhexanol. The addition of 2.0 moles of the alcohol to one mole of DEAC completely forms the dialkoxyl aluminum chloride. The decomposition resulting from adding an excess (3.0 moles of alcohol/mole of aluminum) and the stoichiometric amount (2.0 moles of alcohol/mole of aluminum) are shown in Table 6. An additional experiment was undertaken with a slight decrease in the amount of alcohol (1.9 moles of alcohol/mole of aluminum) to make sure that no excess alcohol would be present due to weighing errors. The results of these runs are also shown in Table 6. Low temperatures were used in this comparison to minimize any thermal decomposition. The temperatures of the experiments are not exactly similar due to the difference in the composition of the kettle and the recycled overhead. The data in the table is from an analysis of the recycled overhead after heating for 14 hours on stream.

TABLE 6

Effect of the Amount of Alcohol on DEAC Alkoxide Decomposition

| Moles Alcohol/Mole Aluminum | 3.0 | 2.0 | 1.9 |
|---|---|---|---|
| Residence Time (in hours) | 14 | 14 | 14 |
| Kettle Temperature (° C.) | 165-170 | 165-167 | 162-163 |
| Overhead Temperature (° C.) | 158 | 158 | 152 |

TABLE 6-continued

Effect of the Amount of Alcohol on DEAC Alkoxide Decomposition

| Composition by GC (%) | | | |
|---|---|---|---|
| 3-Methyleneheptane | 0.067 | 0.02 | 0.017 |
| Octenes | 0.595 | 0.053 | 0.029 |
| Ethylbenzene | 77.065 | 81.527 | 85.352 |
| Decenes | 0.045 | 0.241 | 0.000 |
| Decane | 6.239 | 6.070 | 5.062 |
| 2-Ethylhexanol | 4.509 | 0.000 | 0.000 |
| Dodecane | 10.976 | 10.493 | 8.645 |
| Total | 99.496 | 98.404 | 99.105 |
| Acid Required for Titration (mL) | 22.0 | 245.8 | 245.6 |
| % Decomposition to HCl | 9.04 | 0.05 | 0.06 |

When a 1.0 mole excess of alcohol/mole of aluminum was added to the DEAC the pH paper in contact with the overhead turned acidic quickly and with time the base bath scrubber of the nitrogen purge was neutralized. Significant amounts of octenes and alcohol were observed in the overhead product. The effect of excess alcohol appears to be much stronger than the effect of temperature as thermal decomposition is not observed until close to 190° C. The thermal effect is shown in Table 7 and even at 191° C. (376° F.) the amount of acid formed is much less. An estimate of the amount of decomposition path that forms acid can be made from the amount of acid found in the base bath. The amount of acid would indicate that 9% of the alkoxide formed from pure DEAC was decomposed. This estimate should be considered a minimum for the amount of decomposition as other decomposition products are formed in addition to the acid gas. Using the formation of octenes as an indicator, the time required for the DEAC alkoxide decomposition due to excess alcohol can be estimated. Significant decomposition at these temperatures does not occur in the first two hours and appears to be significant after 6 hours for the case with 3.0 mole of alcohol/mole of aluminum. The term "delta" when used in the Tables and Figures, means the difference between the amount of the referenced material found in the first sample taken, as soon as the overhead starts, from the amount of the same referenced material determined at each of the 2 hour sample intervals. The importance of regulating the alcohol deactivation agent amount to avoid corrosion is apparent. It should also be noted that too little alcohol will also result in active alkyl aluminum being sent for disposal.

Temperature Effects

Thermal decomposition of the deactivated catalyst is of concern since the deactivated catalyst will be exposed to the temperature of the reboilers in the distillation columns. To assess the temperature stability of the alkoxide formed from DEAC and 2-ethylhexanol a temperature decomposition profile was examined. The experiments were done with 2.0 moles of alcohol/mole of aluminum. The results are shown in Table 7.

TABLE 7

DEAC Alkoxide Decomposition Temperature

| Hours on Stream | 14 | 14 | 14 | 14 |
|---|---|---|---|---|
| Kettle Temperature (° C.) | 167 | 175 | 187 | 191 |
| Overhead Temperature (° C.) | 158 | 161 | 172 | 175 |
| Composition by GC (%) | | | | |
| 3-Methylheptane | 0.000 | 0.074 | 0.400 | 0.000 |
| 3-Methyleneheptane | 0.020 | 0.015 | 0.070 | 0.098 |
| Octenes | 0.053 | 0.018 | 0.485 | 0.682 |

TABLE 7-continued

DEAC Alkoxide Decomposition Temperature

| Ethylbenzene | 81.527 | 78.507 | 67.552 | 57.998 |
|---|---|---|---|---|
| Decenes | 0.241 | 0.000 | 0.079 | 0.147 |
| Decane | 6.070 | 7.097 | 9.631 | 10.959 |
| 2-Ethylhexanol | 0.000 | 0.040 | 0.000 | 0.129 |
| Dodecane | 10.493 | 13.987 | 21.365 | 28.694 |
| Total | 98.404 | 99.738 | 99.582 | 98.707 |
| Acid Required for Titration (mL) | 245.8 | | 243.2 | 226.6 |
| % Decomposition | 0.05 | | 0.04 | 0.71 |

Alkoxide decomposition, as measured by the formation of octenes and alcohol is minimal below a temperature of 175° C. and a residence time of less than 14 hours on stream. Octenes are seen to increase significantly by 187° C. but alcohol is not observed until 190° C. The formation of acid is not measurable until 190° C. by titration of the base bath scrubbing the nitrogen purge but the pH paper in contact with the overhead indicates the formation of small amounts of acid even at the lower temperatures. At 190° C. the amount of decomposition due to acid formation is <1%. This is much lower than the decomposition due to acid formation with excess alcohol at 163-170° C. which was 9%.

The composition of the overhead changes with the temperature of the kettle. This is required as some of the lighter components needed to be taken overhead in order to allow the kettle temperature to rise to the desired temperature. In order to determine the amount of each component formed during the experiments at different kettle temperatures, the delta amounts (difference between the 1st overhead sample and last overhead sample) were calculated. These are shown in Table 8. It can be seen that the same conclusions are made from the data in both Table 7 and Table 8. FIG. 1 also illustrates the effect of temperature on decomposition of the aluminum alkoxide resulting from catalyst deactivation (the "aluminum alkoxide") for a mixture in which 2.0 equivalents of alcohol is used to deactivate the oligomerization catalyst.

TABLE 8

DEAC Alkoxide Decomposition Temperature

| Hours on Stream | 14 | 14 | 14 | 14 |
|---|---|---|---|---|
| Kettle Temperature | 167 | 175 | 187 | 191 |
| Delta % - GC Difference from 1st Sample | | | | |
| 3-Methylheptane | 0.000 | 0.056 | 0.400 | 0.000 |
| 3-Methyleneheptane | 0.012 | 0.015 | 0.070 | 0.098 |
| Octenes | −0.001 | −0.039 | 0.397 | 0.468 |
| Ethylbenzene | −1.272 | −1.957 | −2.326 | −6.525 |
| Decenes | 0.211 | 0.000 | 0.028 | 0.055 |
| Decane | 0.941 | 0.426 | 0.456 | 0.621 |
| Alcohol | 0.143 | 0.040 | 0.000 | 0.040 |
| Dodecane | 1.813 | 1.435 | 0.991 | 4.410 |

Table 6 and Table 7 detail the results after 14 hours of heating. To assess the effect of time at each of the temperatures the results from analysis of the samples taken every two hours is plotted. It was seen that decomposition started between 175° C. and 185C. It was observed that significant decomposition did not occur until the 4th hour of heating even at the temperature of 191° C. FIG. 2 also illustrates the effect of residence time, at a number of different temperatures, on decomposition of the aluminum alkoxide for a mixture in which 2.0 equivalents of alcohol is used to deactivate the oligomerization catalyst.

Thermal Decomposition in the GC

A comparison of the GC results of kettle samples with overhead samples showed large differences in the amounts of octenes and alcohol observed. This comparison is shown in Table 9.

TABLE 9

GC Comparison of Overhead and Kettle Samples

| Starting Aluminum Alkyl | DEAC Overhead | DEAC Kettle | TEA Overhead | TEA Kettle |
|---|---|---|---|---|
| GC Analysis Sample # | 8 | 3 | 8 | 3 |
| Time (hours on stream) | 14 | 14 | 14 | 14 |
| Moles of OH/Moles of Al | 1.9 | 1.9 | 3.0 | 3.0 |
| Kettle Temperature (° C.) | 163 | 65 | 192 | 37 |
| Overhead Temperature (° C.) | 152 | 24 | 176 | 24 |
| Composition by GC (%)* | | | | |
| 3-Methylheptane | 0.000 | 0.000 | 0.000 | 0.567 |
| 3-Methyleneheptane | 0.017 | 0.491 | 0.017 | 0.469 |
| Octenes | 0.029 | 2.956 | 0.067 | 4.408 |
| Ethylbenzene | 85.352 | 36.226 | 63.134 | 9.005 |
| Decenes | 0.198 | 0.084 | 0.093 | 0.087 |
| Decane | 5.062 | 6.472 | 10.196 | 4.986 |
| 2-Ethylhexanol | 0.000 | 9.189 | 0.616 | 29.416 |
| Dodecane | 8.645 | 43.206 | 25.606 | 50.416 |
| Total | 99.320 | 98.624 | 99.729 | 99.354 |

*GC injector temperature was 275° C.

When 1.9 moles of alcohol/aluminum was added to DEAC and the resulting mixture heated to 163° C., no alcohol formation was observed in the overhead and only small amounts of octenes were detected. However, when the kettle sample containing the aluminum alkoxide was injected into the GC significant amounts of both the alcohol and octenes were observed. It is reasonable to expect that these materials were observed from the decomposition of the aluminum alkoxide in the GC injector. This effect was confirmed by the observation of a similar pattern when 3.0 moles of alcohol/aluminum was added to TEA. Only small amounts of alcohol and octenes were observed in the overhead sample when the mixture was heated to 192° C. but significant amounts of both these materials were observed in the kettle sample. These observations are consistent with thermal decomposition of the aluminum alkoxide in the GC injection port. The thermal decomposition of aluminum alkoxides provides both alcohol and octenes as products.

Since it was noticed that aluminum alkoxide formed from DEAC decomposition occurring in the GC injection port, it appeared that the temperature of decomposition could also be assessed in this manner. A temperature profile of the effect of the injector port temperature on alcohol and octene formation was undertaken. Only low levels of alcohol and octenes were observed below 175° C. Octene levels increased rapidly between 185° C. and 195° C. and appeared to be complete by 200° C. If one assumes that complete decomposition has occurred above 200° C., then the average values of octene formed between 200° C. and 275° C. would represent 100% alkoxide decomposition. This may allow calculation of the extent of decomposition at the lower temperatures.

Since the temperature of decomposition for aluminum alkoxide formed from TEA appeared to be different than that formed from DEAC, it appeared that a temperature profile of the TEA generated alkoxide could assess this difference. It was seen that the decomposition was much more gradual for the TEA formed alkoxide than for the DEAC formed alkoxide. A tailing alcohol peak at the lower injector port temperatures was also indicative of a decomposition of the alkoxide in the injector port. If one assumes that complete decomposition has occurred at 275° C. and represents 100% alkoxide decomposition. Then calculation of the extent of decomposition at the lower temperatures may be made.

Effect of Water

The addition of water to the dialkoxide of DEAC has a dramatic effect on the production of octenes and acid gas. This effect is shown in Tables 10 and 11. The amount of octenes formed when water is added, at low temperature (162° C.), is similar to the amount of octene formed without water addition at the higher temperature of 191° C. When water was added, acid gas formation was also seen in the change in the pH paper as the initial overhead product caused the pH paper to turn purple as soon as the overhead contacted the paper. This is in contrast to the run without water where only a slight darkening of the pH paper was observed throughout the total run. In the case of water addition at the higher temperature the pH paper turned black and the wire holding the paper in place corroded in half. The initial overhead product taken to control the temperature in the case where water was added contained octenes (1.097%) and alcohol (1.333%) whereas the initial overhead without water contained neither octenes nor alcohol. The presence of alcohol was observed, in the overhead, during the run when water was present but was not observed in the control run at 191° C. without water. It is observed that significant amounts of octenes are only formed after two hours. The amount of octenes formed during the run is approximately the same for the low temperature run with water and the high temperature run without water. This is contrasted with the high temperature run with water which contains 40% octenes which is actually sufficient to reduce the kettle temperature towards the end of the run.

TABLE 10

Effect of Water on DEAC Alkoxide Decomposition as Measured in Overhead Product

| Water Added | 2 g | 2 g | 0 g |
|---|---|---|---|
| Hours on Stream | 14 | 14 | 14 |
| Kettle Temperature (° C.) | 162 | 177 | 191 |
| Overhead Temperature (° C.) | 151 | 162 | 175 |
| Composition by GC (%) | | | |
| Total Octenes | 1.598 | 39.901 | 1.818 |
| Ethylbenzene | 87.511 | 38.991 | 59.384 |
| Decane | 3.373 | 5.532 | 10.699 |
| 3-Chloromethylheptane | 0.000 | 0.276 | 0.000 |
| 2-Ethylhexanol | 0.800 | 2.135 | 0.000 |
| Dodecane | 5.672 | 11.640 | 27.733 |
| Total | 98.953 | 98.475 | 99.634 |

A solid was formed (30.6 g) during the run with water. Some analysis of this dried solid was done to attempt to get a possible structure. It was found by X-ray to have 25.9% aluminum and 17.1% chloride. There were no alumina bands in the X-ray diffraction analysis and C, H, N, S analysis showed 7.23% carbon and 5.64% hydrogen.

TABLE 11

Effect of Water and Temperature on DEAC Alkoxide Decomposition

| Water Added (g) | 0.66 | 0.60 | 0.57 |
|---|---|---|---|
| Moles Alcohol/Mole Metal | 2.0 | 2.0 | 2.0 |
| Hours on Stream | 14 | 14 | 14 |
| Average Kettle Temp (C.) | 177 | 190 | 197 |
| % Total Octenes | 1.61 | 5.34 | 26.12 |
| % 2,5-Dimethylpyrrole | 0 | 0 | 0 |
| % 2-Ethylhexanol | 0 | 0.52 | 0.578 |
| % Decomposition to HCl | 0.19 | 0.70 | 3.90 |

FIG. 3 also illustrates the effect of water in the catalyst deactivation agent on the temperature at which octenes are formed as a result of the aluminum alkoxide decomposition.

While this invention has been described in detail for the purpose of illustration, it is not to be construed as limited thereby but is intended to cover all changes and modifications within the spirit and scope thereof.

What is claimed is:

1. A process to deactivate a halide-containing olefin oligomerization catalyst system and inhibit or limit the decomposition of the deactivated catalyst system during recovery of an olefin oligomerization product comprising the steps of:
   a) contacting an alcohol with an adsorbent capable of adsorbing water;
   b) forming an intermediate stream by contacting an olefin oligomerization reactor effluent stream which comprises olefin product(s), catalyst system, and heavies with the alcohol thereby deactivating the catalyst system; and
   c) separating the intermediate stream of step (b) into at least one olefin oligomerization product stream and at least one heavies stream;
   wherein the separation comprises a distillation comprising a reboiler and material passed through the reboiler is maintained below about 190° C., and
   wherein said catalyst system comprises a chromium source, a pyrrole-containing compound and an alkylaluminum compound and wherein the alcohol is soluble in any portion of the reactor effluent stream.

2. A process according to claim 1 wherein said reactor effluent stream comprises olefin product(s); the olefin oligomerization catalyst system; an organic diluent; one or more mono-olefins; and heavies.

3. A process according to claim 1 wherein the olefin oligomerization catalyst system comprises a halide compound and an alkylaluminum compound.

4. A process according to claim 1 wherein the olefin oligomerization catalyst system comprises a halogenated alkylaluminum compound.

5. A process according to claim 1 wherein the olefin oligomerization catalyst system comprises a mixture of an alkylaluminum compound and a halogenated alkylaluminum compound.

6. The process of claim 4 wherein the halogenated alkylaluminum compound is diethylaluminum chloride.

7. The process of claim 1 wherein the alcohol has a boiling point different from the olefin product in the reactor effluent stream.

8. The process of claim 1 wherein the alcohol has 6 or more carbon atoms per molecule.

9. The process of claim 1 wherein the alcohol is selected from the group of 1-hexanol, 3-hexanol, 2-ethyl-1-hexanol, 3-octanol, 1-heptanol, 2-heptanol, 3-heptanol, 4-heptanol, 2-methyl-3-heptanol, 1-octanol, 2-octanol, 4-octanol, 7-methyl-2-decanol, 1-decanol, 2-decanol, 3-decanol, 4-decanol, 5-decanol, 2-ethyl-1-decanol, and mixtures thereof.

10. The process of claim 1 wherein the alcohol is selected from the group of diols and polyols.

11. The process of claim 1 wherein material passed through the reboiler is maintained below 175° C.

12. The process of claim 1 wherein the distillation process includes at least two distillation stages.

13. The process of claim 1 wherein the alkylaluminum compound is a mixture of triethylaluminum and diethyl aluminum chloride, the alcohol is 2-ethyl-1-hexanol, and the olefin product comprises 1-hexene.

14. The process of claim 1 wherein the olefin oligomerization product stream comprises one or more olefin trimers.

15. A process of claim 1, wherein the separation comprises at least two distillation stages and material passed through each reboiler is maintained below about 190° C.

* * * * *